United States Patent [19]
Anderson et al.

[11] Patent Number: 5,648,588
[45] Date of Patent: Jul. 15, 1997

[54] METHOD FOR REMOVING SULFONE AND HYDROGEN FLUORIDE FROM A HYDROCARBON STREAM AND PRODUCING A SULFONE PRODUCT FREE OF HYDROGEN FLUORIDE

[75] Inventors: Richard L. Anderson; Bruce B. Randolph, both of Bartlesville, Okla.

[73] Assignee: Phillips Petroleum Company, Bartlesville, Okla.

[21] Appl. No.: 569,625

[22] Filed: Dec. 8, 1995

[51] Int. Cl.[6] .................................................. C07C 2/62
[52] U.S. Cl. .......................... 585/724; 585/719; 585/704; 585/723
[58] Field of Search ...................................... 585/724, 723, 585/704, 719

[56] References Cited

U.S. PATENT DOCUMENTS

| | | | |
|---|---|---|---|
| 5,264,649 | 11/1993 | Eastman | 585/80 L |
| 5,306,859 | 4/1994 | Eastman et al. | 585/724 |
| 5,347,065 | 9/1994 | Anderson | 585/724 |

*Primary Examiner*—Helane Myers
*Attorney, Agent, or Firm*—Charles W. Stewart

[57] ABSTRACT

Disclosed is a process for separating sulfone and hydrogen fluoride from hydrocarbon streams containing a concentration of such compounds. An extraction solvent laden with sulfone and HF is contacted with a reversible base in order to remove the HF therefrom. The thus-treated extract stream is separated into a water stream that can be reused as the water extractant and a sulfone stream that is suitably free of HF.

12 Claims, 2 Drawing Sheets

METHOD FOR REMOVING SULFONE AND HYDROGEN FLUORIDE FROM A HYDROCARBON STREAM AND PRODUCING A SULFONE PRODUCT FREE OF HYDROGEN FLUORIDE

The present invention relates to a process for removing sulfone and hydrogen fluoride from a hydrocarbon stream containing a concentration of such compounds and producing a sulfone substantially free of hydrogen fluoride.

It has recently been discovered that sulfone additives can be utilized in combination with traditional hydrogen fluoride alkylation catalysts as a means for providing an alkylation catalyst having a low volatility. One side effect from utilizing a sulfone additive in combination with a hydrofluoric acid alkylation catalyst is that small concentrations of sulfone become dissolved in the alkylate product from a hydrofluoric acid catalyzed alkylation process. The small concentration of sulfone in the alkylate product can have a negative impact on the alkylate as a gasoline blend component. Thus, even though the concentration of sulfone is very small, it is desirable to remove such small concentration of sulfone from the alkylate product in order to prevent its negative economic consequences on refiners who use the alkylate as a gasoline blending component.

Another concern with treating an alkylate product from a hydrofluoric acid catalyzed alkylation process is the removal of dissolved hydrofluoric acid (also referred to herein as "HF"). Hydrogen fluoride must be removed from the alkylate product in order for it to be suitable for use as a gasoline blending component.

One method for removing sulfone and hydrogen fluoride from an alkylate reaction product containing such compounds is to use water as an extraction solvent. But, while water can serve as an effective extraction solvent, the presence of hydrogen fluoride makes it difficult to produce a final sulfone product that is substantially free of these compounds or to recover for reuse the water extractant that is free of hydrogen fluoride. A further concern is the highly corrosive nature of water having a small concentration of HF. The handling of such a fluid requires the use of special metallurgical materials.

It is, thus, an object of this invention to provide a method for removing sulfone that is contained in an alkylate reaction product.

It is a further object of this invention to provide a method for separating a small concentration of sulfone contained in an alkylation reaction product which contains a concentration of such sulfone.

A yet further object of this invention is to provide a method for producing a sulfone product that is substantially free of hydrogen fluoride.

A still further object of this invention is to provide for the removal of sulfone and HF from an alkylate reaction product having a concentration of sulfone and HF and subsequently producing a sulfone product that is substantially free of HF.

Thus, the process of the present invention includes removing sulfone and hydrogen fluoride from a hydrocarbon stream having a concentration of such compounds and producing a sulfone product that is free of hydrogen fluoride. This process includes extracting the sulfone and HF from the hydrocarbon stream by contacting such hydrocarbon stream with water. The water serves as an extraction solvent by extracting at least a portion of the sulfone and HF contained in the hydrocarbon stream and providing an extract stream comprising water enriched with sulfone and HF. A hydrocarbon raffinate stream is produced having a concentration of sulfone and HF that is smaller than the concentration of sulfone and HF in the original hydrocarbon stream contacted with the extraction solvent. The extract stream is contacted with a reversible base under conditions suitable for the removal of at least a portion of the HF in the extract stream to provide a treated extract stream substantially free of HF. Water is separated from the sulfone of the treated extract stream, which is substantially free of HF, to provide a water stream, comprising water, and a sulfone stream, comprising sulfone. The water stream may be reused as the extraction solvent.

An additional embodiment of the invention relates to a method for removing sulfone and HF from a hydrocarbon stream having a sulfone concentration exceeding about 100 parts per million weight (ppmw) and an HF concentration exceeding about 0.5 ppmw. The hydrocarbon stream is contacted with a water solvent. An extract stream enriched with sulfone and HF and comprising water is recovered. Also recovered is a raffinate stream comprising the hydrocarbon of the hydrocarbon stream and having a reduced concentration of sulfone and HF below that of the sulfone and HF concentration of the hydrocarbon stream. The extract stream is contacted with a reversible base under conditions suitable for the removal of at least a portion of the HF in the extract stream to provide a treated extract stream substantially free of HF. Water is separated from the sulfone of the treated extract stream, which is substantially free of HF, to provide a water stream, comprising water, and a sulfone stream, comprising sulfone. The water stream can be reused as the extraction solvent.

Figure 1:
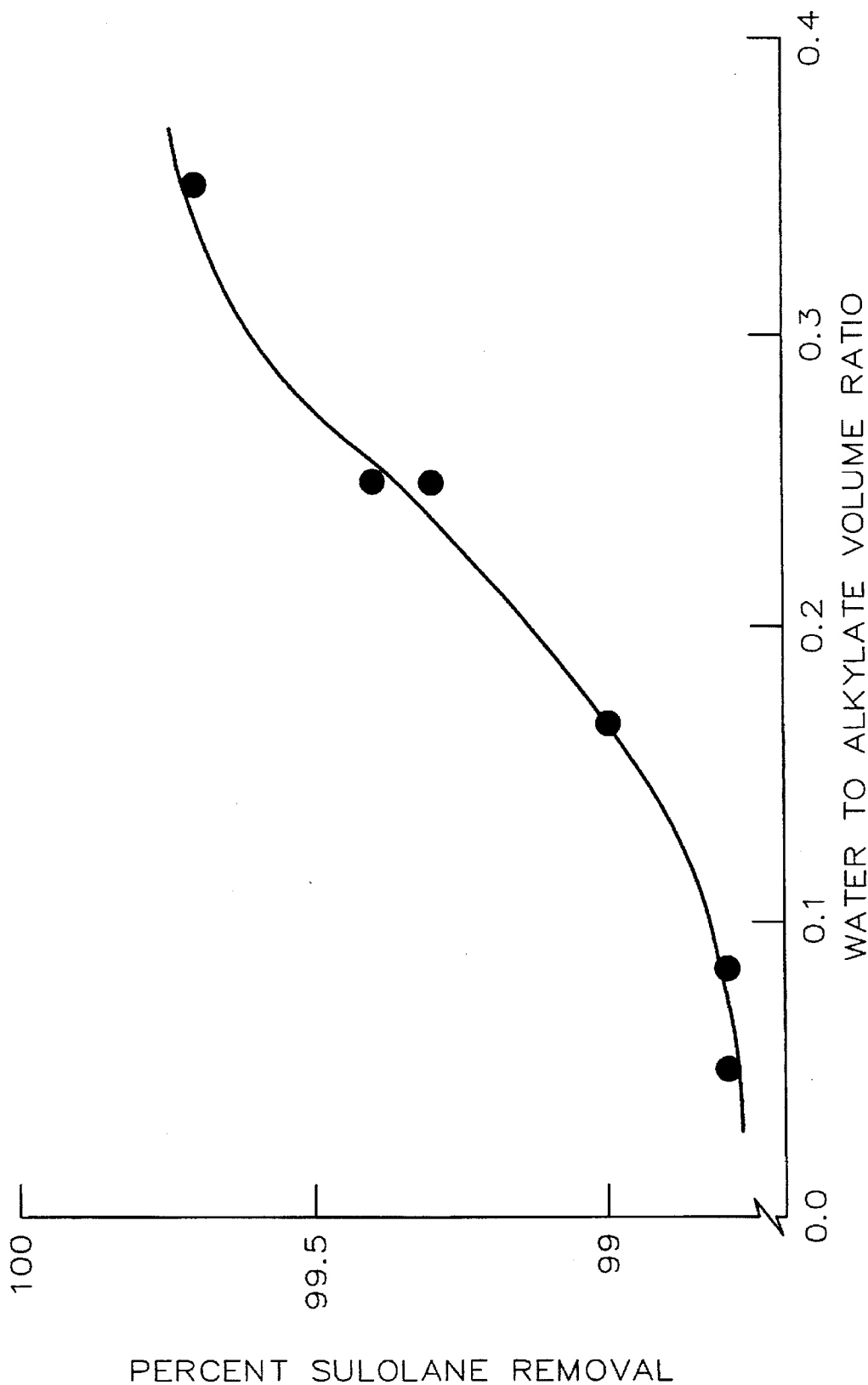
FIG. 1 is a plot of extraction data for water as an extractant for removing sulfolane from alkylate.

The process of this invention contemplates the resolution of problems associated with a gasoline blending component containing a small concentration of a sulfone compound. This sulfone compound, in sufficient concentrations, serves as a contaminant to a gasoline end-product when it is contained in a gasoline blending component such as an alkylate product produced by the catalytic alkylation of olefins and isoparaffins. In particular, it has recently been discovered that a novel catalyst which utilizes a sulfone as one component in combination with hydrogen fluoride can provide for a suitable alkylate product. One problem encountered, however, is that when utilizing a mixture of the hydrogen fluoride and sulfone as an alkylation catalyst, due to the slight solubility of sulfone in hydrocarbon, there is a small concentration of the sulfone that passes from the alkylation reaction system along with the alkylate end-product. It is, thus, critical for a significant portion of the sulfone contained in the alkylate end-product to be removed prior to utilizing it as a gasoline blending component.

The need to remove the sulfone concentration is important even though the sulfone is only slightly soluble in the alkylate hydrocarbon with the concentration levels generally not exceeding 10,000 parts per million weight (ppmw) of the alkylate product. Typically, the sulfone will be present in the alkylate product at a concentration in the range from about 100 to about 10,000 ppmw. More typically, the sulfone concentration in the alkylate product is in the range from about 200 to about 5000 ppmw and, most typically, it will be in the range from 250 to 3000 ppmw.

Another concern with the treatment of the alkylate from an HF catalyzed alkylation process is the presence of HF dissolved in the alkylate end-product and the removal of such therefrom. An alkylate product is an unsuitable gasoline blend stock when HF is present; therefore, it must be removed to give a treated alkylate product having a concentration of hydrogen fluoride less than that of the untreated alkylate product.

It is, therefore, important to remove a significant portion of the sulfone and HF concentration in a hydrocarbon stream containing such compounds. Generally, it is necessary for at least a portion of the sulfone and HF to be removed from the hydrocarbon stream. The portion of sulfone and HF removed from the hydrocarbon stream can be at least about 70 weight percent of the concentration of sulfone and HF. Preferably, it is desirable to remove at least about 80 weight percent of the sulfone and HF contained in the hydrocarbon stream and, most preferably, it is desirable to remove at least 90 weight percent. In fact, the novel process described herein has the exceptional ability under proper process conditions of removing at least 99 weight percent of the sulfone and HF contained in the hydrocarbon stream when the concentration of each of these compounds is less than about 1 weight percent.

The hydrocarbon stream of the invention generally will include hydrocarbons having from 3 to 12 carbon atoms and with the most common hydrocarbons being isoparaffins. Specifically, the hydrocarbon stream will be an alkylate hydrocarbon product comprising isoparaffins produced by the catalytic reaction of olefins and isoparaffins of an alkylation process. The alkylation catalyst utilized in the alkylation process comprises a sulfone component and hydrogen fluoride. The alkylation catalyst utilized in the alkylation of the olefins and isoparaffins generally will have a weight ratio of hydrogen fluoride to sulfone in the range of about 1:1 to about 40:1. A preferred weight ratio of hydrogen fluoride to sulfone in the alkylation catalyst can range from about 2.3:1 to about 19:1 and, more preferably, it can range from 3:1 to 9:1.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant, and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

The sulfones suitable for use are the sulfones of the general formula

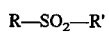

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone (tetrahydrothiophene-1,1-dioxide) or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

Because of a slight solubility of sulfone in the alkylate hydrocarbon product, its concentration therein will be small. Generally, the sulfone concentration of the alkylate hydrocarbon product does not exceed 10,000 ppmw and, specifically, it can range from about 100 ppmw to about 10,000 ppmw depending on processing conditions. Ordinarily, the sulfone concentration in the alkylate hydrocarbon product can range from about 200 ppmw to about 5000 ppmw and, most likely, it can range from 250 ppmw to 3000 ppmw.

Hydrogen fluoride is also slightly soluble in the alkylate product generally being present at a concentration of less than about 20 ppmw of the alkylate hydrocarbon product. Specifically, the concentration of HF in the alkylate product can range from about 0.1 ppmw to about 10 ppmw. More specifically, the concentration range of HF in the alkylate product can range from about 0.25 ppmw to about 5 ppmw and, most specifically, it can range from 0.5 to 2 ppmw.

Because of the contamination caused by an excessive concentration of sulfone and HF in the alkylate hydrocarbon product, it is desirable to remove at least a portion of these compounds so as to have a gasoline blending component that can suitably be blended with other gasoline components to produce a desirable gasoline end-product. Thus, a substantial portion of the sulfone and HF content of the alkylate hydrocarbon product is removed by the inventive process which is capable of removing at least about 70 weight percent of such compounds contained in the alkylate hydrocarbon product. Preferably, it is desirable to remove at least about 80 weight percent of the sulfone and HF content of the alkylate hydrocarbon product and, most preferably, it is desirable to remove at least 90 weight percent of the sulfone and HF content. Because of the efficiency of the process of this invention, it is even possible, under appropriate process conditions, to remove upwardly to 99 weight percent, or more, of the sulfone contained in the hydrocarbon alkylation product and to give a hydrocarbon alkylation product that is substantially free of sulfone and HF.

The alkylate hydrocarbon product is contacted with an extraction solvent comprising, consisting of, or consisting essentially of, water. Any suitable contacting means for contacting the extraction solvent with the alkylate hydrocarbon product can be used for providing intimate mixing or contacting of the extraction solvent with the alkylate hydrocarbon product. Such contacting means as plate columns, packed columns or single stage contacting means, which include static mixers and mechanically agitated vessels, may be used. Thus, any means which provides for the intimate contacting or mixing of the extraction solvent with the alkylate hydrocarbon product may be used as a part of this invention.

Any amount of extraction solvent relative to the quantity of the alkylate hydrocarbon product can be utilized in the process provided the amount of extraction solvent contacted with the alkylate hydrocarbon product is effective for the removal of at least a portion of the sulfone and HF contained in the alkylate hydrocarbon product. Preferably, the extraction solvent is to remove substantially all of the sulfone and HF contained in the alkylate hydrocarbon product. Generally, contacting efficiency requires an amount of extraction solvent relative to the alkylate hydrocarbon product such that the volumetric ratio of water contacted with the alkylate hydrocarbon is at least about 0.02:1 water to hydrocarbon. Preferably, the volumetric ratio of water contacted with hydrocarbon is at least about 0.05:1 and, most preferably, the volumetric ratio can exceed 0.08:1. Economics will generally set the upper limit for the volumetric ratio of water to alkylate hydrocarbon product.

An extract stream, comprising water and enriched with sulfone and HF, is recovered from the contacting means. The extract stream will contain at least a portion of the sulfone and HF contained in the alkylate hydrocarbon product and can contain, as earlier described herein, at least about 70 weight percent of the sulfone and HF contained in such alkylate hydrocarbon product.

The extract stream will generally contain upwardly to about 100,000 ppmw surfone; but, specifically, the concentration range of sulfone in the extract stream will be in the range from about 250 ppmw to about 90,000 ppmw. More specifically, the sulfone concentration in the extract stream is in the range from 500 ppmw to 8,000 ppmw.

The concentration of HF in the extract stream will vary depending upon the amount of HF in the alkylate hydrocarbon product, but it can be upwardly to about 1,000 ppmw. Typically, however, the concentration of HF in the extract stream can be in the range from about 0.5 ppmw to about 700 ppmw. More typically, the HF concentration in the extract stream can be in the range of from 2 ppmw to 30 ppmw.

The water concentration of the extract stream generally exceeds about 95 weight percent. Specifically, the water concentration in the extract stream can be in the range of from about 97 weight percent to about 99.75 weight percent. Most specifically, the water concentration can be in the range of from 98 weight percent to 99.5 weight percent.

Also recovered from the contacting means is a raffinate stream comprising the alkylate hydrocarbon product having a reduced sulfone concentration below that of the alkylate hydrocarbon product. Generally, the sulfone concentration of the raffinate stream can be less than about 250 ppmw. Preferably, however, the concentration of sulfone in the raffinate stream can be less than 200 ppmw and, most preferably, the concentration sulfone in the raffinate stream is less than 100 ppmw.

The concentration of HF in the extract stream poses problems associated with the separation and recovery of the water extractant and the sulfone, and it causes equipment corrosion. Water having a small concentration of HF is quite corrosive when exposed to carbon steel process equipment; therefore, the HF needs to be removed to protect such equipment. Moreover, the sulfone separated from the extract stream needs to have the HF removed from it for it to be a suitable product. Thus, it is necessary for the extract stream to be processed so as to remove the HF contained therein.

A novel aspect for removing HF from the extract stream, comprising water, sulfone and HF is to contact such extract stream with a suitable reversible base to thereby remove a portion, preferably a substantial portion, of the HF contained in the extract stream. This removal step is important so that the subsequent separation of the sulfone from the water extractant can provide a sulfone product that is substantially free of HF, and it is important for minimizing the corrosion of carbon steel process equipment.

Suitable reversible bases for removing HF from the extract stream include those selected from the group consisting of polyvinylpyridine, amine substituted styrene divinylbenzene copolymer and mixtures thereof. The polyvinylpyridine materials or resins and the amine substituted styrene divinylbenzene copolymer materials or resins useful as reversible bases in the invention, thus, generally include styrene/divinylbenzene copolymers on which nitrogen-containing groups are attached during or after polymerization. The basic functional groups are attached to the polymer backbone by either carbon-carbon bonds, for example, polyvinylpyridine, or by carbon-nitrogen bonds, for example, dialkylamine or trialkylammonium hydrohalide resins. The basic functional groups are incorporated into the polymer by any conventional technique known in the art. The preferred reversible bases for use in the invention are those polymers that are in solid particulate form at standard conditions and which are selected from the group consisting of polyvinylpyridine, amine substituted styrene divinyl benzene copolymer and mixtures thereof. The most preferred reversible bases, however, are those selected from the group consisting of poly-(2-vinylpyridine), poly-(4-vinylpyridine), and mixtures thereof.

Generally, the extract stream is contacted with the reversible base under suitable process conditions for removing HF from the extract stream. The contact material contemplated for use by this invention is in the form of solid particulate material and can be contained as a bed within a vessel defining a contacting zone in which the extract stream can be contacted with the contact material. However, this invention is not confined to the use of standard vessels for defining a contacting zone, but any suitable means known in the art can be utilized for contacting the extract stream with the contact material. The thus-treated extract stream can have a substantially reduced concentration of HF below that of the extract stream. Preferably, the treated extract stream is substantially free of HF having an HF concentration of less than 0.1 ppmw and approaching zero.

The treated extract stream that is preferably substantially free of HF is passed to separation means for separating the water and sulfone to provide a water stream, comprising water, and a sulfone stream, comprising sulfone. Any suitable type of separation means may be used to define a separation zone. Standard fractionation methods are preferred for providing the water stream and the sulfone stream. Because the HF is substantially removed from the extract stream prior to the separation of the treated extract stream, both the sulfone stream and the water stream are substantially free of HF. The water stream can be used as the water extractant for removing sulfone and HF from the alkylate hydrocarbon product.

Figure 2:
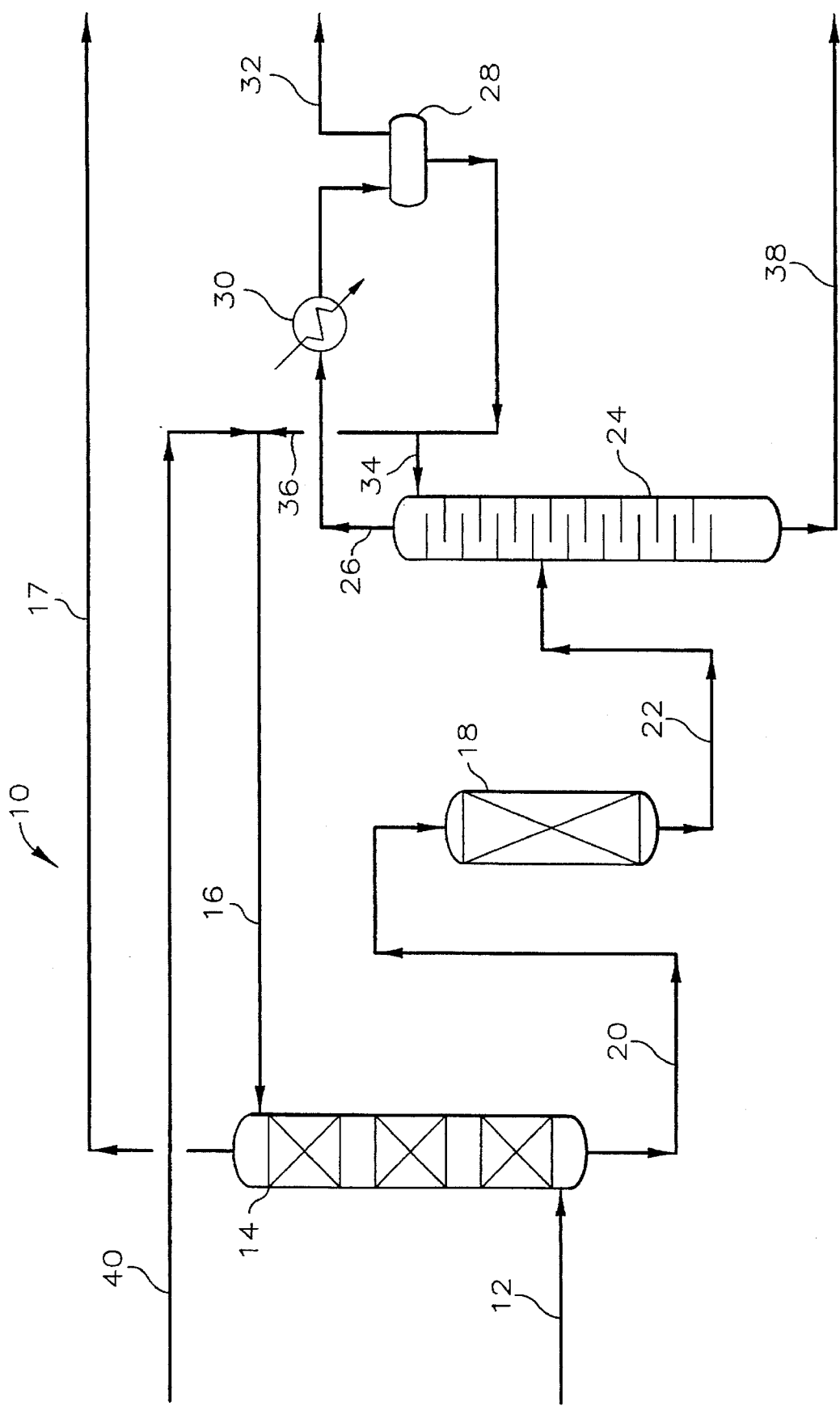
FIG. 2 provides a schematic representation of the process which is one embodiment of the invention.

Referring now to FIG. 2, there is presented a schematic representation of process system 10, which depicts a liquid-liquid extraction process system utilized for the extraction of a sulfone solute and an HF solute from an alkylate hydrocarbon product stream and other separation equipment for producing a sulfone product substantially free of HF. The alkylate hydrocarbon product stream, which comprises an alkylate product having a concentration of sulfone and HF, passes by way of conduit 12 to extractor 14. Extractor 14 defines a contacting zone and provides contacting means for contacting the alkylate hydrocarbon product stream with an extraction solvent comprising water. The extraction solvent is introduced into extractor 14 via conduit 16. A raffinate stream, which is the alkylate hydrocarbon product stream having a substantially reduced concentration of sulfone and HF below that of the alkylate hydrocarbon product stream, passes from extractor 14 by way of conduit 17.

Extractor 14 is operably connected in fluid flow communication with contacting vessel 18 by conduit 20. An extract stream is recovered from extractor 14 by way of conduit 20. The recovered extract stream comprises water with at least a portion of the sulfone and HF contained in the alkylate hydrocarbon product and passes to contacting vessel 18. Contacting vessel 18 defines a contacting zone, which contains a reversible base. The contacting zone provides for the contacting of the extract stream with the reversible base to thereby provide a treated extract stream substantially free of HF. Contacting vessel 18 is operatively connected in fluid flow communication by conduit 22 with fractionator 24.

The treated extract stream passes from contacting vessel 18 by way of conduit 22 to fractionator 24. Fractionator 24 defines a separation zone and provides means for separating the treated extract stream into a water stream, comprising water, and a sulfone stream, comprising sulfone. Both the water stream and sulfone stream produced by fractionator 24 are substantially free of HF. Fractionator 24 is preferably a conventional distillation column equipped with a reboiler (not shown) and an overhead system. Overhead vapor from Fractionator 24 passes by way of conduit 26 to overhead accumulator 28. Interposed in conduit 26 is overhead condenser 30 which provides by indirect heat exchange for the condensation of the overhead vapor. In a preferred embodiment, fractionator 24 is operated under vacuum conditions, which is provided for by conduit 32.

The condensed overhead comprises primarily water with a portion passing as a reflux to fractionator 24 by way of conduit 34. The remaining portion of the condensed overhead passes as the water stream by way of conduit 36 to extractor 14 and serves as the water extraction solvent for extractor 14. The sulfone stream passes from fractionator 24 by way of conduit 38. Make-up water may be added to process system 10 through conduit 40.

The following examples are provided to further illustrate the present invention. The examples are provided by way of illustration only. They are not intended as a limitation upon the invention as set out in the appended claims.

EXAMPLE I

Example I presents data obtained from extraction experiments using water as an extraction solvent for removing sulfolane from alkylate. An alkylate feed containing, on average, 1082 ppmw sulfolane was charged to a commercially available one inch, stirred, York-Scheibel extractor containing approximately 8 theoretical stages. The data obtained are present in Table I and are charted in FIG. 1. As the data show, water can be an effective solvent for extracting sulfolane contained in a hydrocarbon solution. The water solvent is effective in removing more than 99 weight percent of the sulfolane contained in an alkylate. The weight percent sulfolane removed increases with increasing water to alkylate ratios.

TABLE I

| Water/Alkylate Ratio (vol/vol) | Sulfolane Removal (weight percent) | Alkylate/Water Ratio (vol/vol) |
|---|---|---|
| 0.050 | 98.8 | 20 |
| 0.083 | 98.8 | 12 |
| 0.167 | 99.0 | 6 |
| 0.250 | 99.3 | 4 |
| 0.250 | 99.4 | 4 |
| 0.330 | 99.7 | 3 |

EXAMPLE II
(CALCULATED)

To illustrate the inventive process of FIG. 1, this calculated example is provided. The material balance of the calculated example is provided in Table II. The stream numbers shown in Table II correspond to those represented in FIG. 2. The alkylate feed to the extractor contains 0.5 ppmw HF and 1082 ppmw sulfolane and is charged to the extractor at an approximate rate of 1950 barrels per day. The recovery of sulfolane in the extractor is based on Table I at a 0.083 vol. water/1 vol. alkylate ratio. The extract phase contains about 4 ppmw HF and, at this level, is sufficient to lower the pH to around 2.5. This would require alloy metallurgy in the sulfolane fractionator if the HF is not removed by the reversible base.

TABLE II

| | Calculated Material Balance | | | | | |
|---|---|---|---|---|---|---|
| Component | Stream 12 lbs/hr | Stream 17 lbs/hr | Stream 20 lbs/hr | Stream 22 lbs/hr | Stream 36 lbs/hr | Stream 38 lbs/hr |
| Alkylate | 19789.00 | 19788.97 | 0.03 | 0.00 | 0.00 | 0.00 |
| Sulfolane | 21.46 | 0.25 | 21.21 | 21.21 | 0.01 | 21.21 |
| HF | 0.01 | 0.00 | 0.01 | 0.00 | 0.00 | 0.00 |
| Water | 0.00 | 3.30 | 2421.13 | 2421.13 | 2424.43 | 0.06 |
| Total | 19810.47 | 19792.52 | 2442.38 | 2442.34 | 2424.44 | 21.27 |
| Temp (F.) | 100 | 99 | 99 | 99 | 95 | 316 |
| Press (psia) | 50 | 50 | 50 | 45 | 65 | 4 |

While this invention has been described in terms of the presently preferred embodiment, reasonable variations and modifications are possible by those skilled in the art. Such variations and modifications are within the scope of the described invention and the appended claims.

That which is claimed is:

1. A process for separating sulfone and HF from a hydrocarbon stream containing a concentration of sulfone and HF, said process comprises:

extracting sulfone and HF from said hydrocarbon stream by contacting said hydrocarbon stream with a water extractant to thereby extract at least a portion of the sulfone and HF contained in said hydrocarbon stream from said hydrocarbon stream and to provide an extract stream, comprising water and enriched with sulfone and HF, and a raffinate stream having a reduced concentration of sulfone and HF below said concentration of sulfone and HF in said hydrocarbon stream;

contacting said extract stream with a reversible base selected from the group consisting of polyvinylpyridine, amine substituted styrene divinylbenzene copolymer and mixtures thereof under conditions suitable for the removal of at least a portion of the HF in said extract stream to thereby provide a treated extract stream substantially free of HF;

separating said treated extract stream into a water stream, comprising water, and a sulfone stream, comprising sulfone; and utilizing said water stream as said water extractant.

2. A process as recited in claim 1 wherein said reduced concentration of sulfone is less than about 250 ppmw and said reduced concentration of HF is substantially zero.

3. A process as recited in claim 2 wherein said at least a portion of said sulfone represents at least about 70 weight percent of said sulfone in said hydrocarbon stream.

4. A process as recited in claim 3 wherein said hydrocarbon stream comprises paraffin compounds.

5. A process as recited in claim 4 wherein said paraffin compounds include paraffins produced by the catalytic reaction of olefins and isoparaffins.

6. A process as recited in claim 5 wherein said sulfone is sulfolane.

7. A process as recited in claim 6 wherein the volumetric ratio of water contacted with said hydrocarbon stream is at least about 0.02:1 water to hydrocarbon.

8. A method for removing sulfone and HF from a hydrocarbon stream having a concentration of sulfone and HF and containing a hydrocarbon, said method comprises:

contacting said hydrocarbon stream, having a sulfone concentration exceeding about 100 ppmw and HF concentration exceeding about 0.5 ppmw with a solvent comprising water;

recovering an extract stream enriched with sulfone and HF;

recovering a raffinate stream comprising said hydrocarbon and having a reduced concentration of sulfone and HF below said concentration of sulfone and HF of said hydrocarbon stream;

contacting said extract stream with a reversible base selected from the group consisting of polyvinylpyridine, amine substituted styrene divinylbenzene copolymer and mixtures thereof under conditions suitable for the removal of at least a portion of the HF in said extract stream to thereby provide a treated extract stream substantially free of HF;

separating said treated extract stream into a water stream, comprising water, and a sulfone stream, comprising sulfone; and utilizing said water stream as said solvent.

9. A method as recited in claim 8 wherein said extract stream contains at least 70 weight percent of said sulfone of said hydrocarbon stream.

10. A method as recited in claim 9 wherein said hydrocarbon is a paraffin compound produced by the catalytic reaction of olefins and isoparaffin.

11. A method as recited in claim 10 wherein said sulfone is sulfolane.

12. A method as recited in claim 11 wherein the volumetric ratio of said solvent contacted with said hydrocarbon stream is at least about 0.02:1 solvent to hydrocarbon.

* * * * *